United States Patent
Houser et al.

(12) 
(10) Patent No.: US 6,241,715 B1
(45) Date of Patent: Jun. 5, 2001

(54) DISPOSABLE THERAPEUTIC BREAST PAD

(76) Inventors: Reid D. Houser; Virginia I. Houser, both of 207 Meadow Dr., Treynor, IA (US) 51575

( * ) Notice: Subject to any disclaimer, the term of this patent is extended or adjusted under 35 U.S.C. 154(b) by 0 days.

(21) Appl. No.: 09/408,424

(22) Filed: Sep. 29, 1999

(51) Int. Cl.[7] .............................. A61F 13/15; A61F 13/20
(52) U.S. Cl. ............... 604/385.07; 604/358; 604/385.01; 450/37; 450/56; 450/57; 450/81
(58) Field of Search ................... 607/108; 2/463; 128/890, 889, 892, 893, 894; 450/36; 602/47, 59; 604/358, 385.07, 385.01

(56) References Cited

U.S. PATENT DOCUMENTS

| | | |
|---|---|---|
| D. 321,058 | 10/1991 | Dickinson . |
| 2,494,987 | 1/1950 | Chaitin . |
| 3,301,254 | 1/1967 | Schickendanz . |
| 4,125,114 * | 11/1978 | Repke ................... 128/280 |
| 5,017,174 * | 5/1991 | Gowrylow ............... 450/37 |
| 5,050,595 * | 9/1991 | Krafft .................... 128/379 |
| 5,133,348 | 7/1992 | Mayn . |
| 5,304,215 * | 4/1994 | MacWhinnie et al. .......... 607/106 |
| 5,456,704 | 10/1995 | Kilcullen . |
| 5,476,490 | 12/1995 | Silver . |
| 5,507,794 * | 4/1996 | Allen ....................... 607/112 |
| 5,679,052 | 10/1997 | Rucki . |
| 5,702,375 | 12/1997 | Angelillo et al. . |
| 5,776,177 * | 7/1998 | MacWhinnie et al. .......... 607/108 |
| 5,810,796 | 9/1998 | Kimura et al. . |
| 5,890,487 | 4/1999 | Kimmel . |
| 5,897,580 | 4/1999 | Silver . |
| 6,063,110 * | 5/2000 | Stedman .................. 607/108 |

* cited by examiner

*Primary Examiner*—Aaron J. Lewis
*Assistant Examiner*—Michele Kidwell
(74) *Attorney, Agent, or Firm*—Zarley, McKee, Thomte, Voorhees & Sease; Dennis L. Thomte

(57) ABSTRACT

A disposable therapeutic breast pad for heating or cooling the female breast during nursing comprising a generally disc-shaped, moisture-impervious outer layer and an absorbent material disposed inwardly of the outer layer adapted to be soaked in hot or cold water so that the breast pad may be positioned adjacent the female breast with the absorbent material in direct contact therewith to heat or cool the female breast during nursing.

5 Claims, 2 Drawing Sheets

DISPOSABLE THERAPEUTIC BREAST PAD

BACKGROUND OF THE INVENTION

1. Field of the Invention

This invention relates to a breast pad and more particularly to a disposable therapeutic breast pad for heating or cooling the female breast to alleviate the symptoms of clogged milk ducts, mastitis or engorgement.

2. Description of the Related Art

Nursing mothers frequently require therapeutic treatment, either hot or cold, to relieve or alleviate clogged milk ducts, mastitis or engorgement. Many different types of hot and cold packs have been provided for heating or cooling the female breast during nursing. However, the prior art hot and cold packs known to applicants normally contain gel packs therein which substantially increases the cost thereof and which results in the breast pads not truly being disposable breast pads. Further, the prior art breast pads known to applicants are not able to be separated into two generally C-shaped breast pad members so that the C-shaped breast pad member may be placed adjacent a portion of the breast rather than the entire breast. Additionally, most of the prior art breast pads contact the nipple, which may irritate the same.

SUMMARY OF THE INVENTION

A disposable hot or cold therapeutic breast pad for heating or cooling the female breast during nursing is described comprising a generally disc-shaped, moisture-impervious outer layer having inner and outer surfaces with an absorbent material disposed inwardly of the inner surface of the outer layer. The breast pad is adapted to be soaked in hot water or ice water so that the breast pad may be positioned adjacent the female breast with the absorbent material in direct contact therewith to heat or cool the female breast during nursing. Preferably, the central portion of the breast pad is provided with an opening formed therein for receiving the nipple of the female breast. Preferably, a perforated tear line extends from one side edge of the breast pad to the other so that the breast pad may be separated into two generally C-shaped breast pad members. When the perforated tear line is employed in the breast pad, it is preferred that upper and lower rows of stitching extend through the breast pad above and below the perforated tear line.

It is a principal object of the invention to provide a disposable therapeutic breast pad for heating or cooling the female breast during nursing.

A further object of the invention is to provide a disposable therapeutic breast pad having a central opening formed therein for receiving the nipple of the female breast.

Still another object of the invention is to provide a disposable therapeutic breast pad comprising a moisture-impervious outer layer and an absorbent material disposed inwardly thereof.

Still another object of the invention is to provide a therapeutic disposable breast pad which is generally disc-shaped, but which may be easily separated into two generally C-shaped breast pad members.

Yet another object of the invention is to provide a disposable therapeutic breast pad which is economical of manufacture for enhancing the disposable nature thereof.

These and other objects of the invention will be apparent to those skilled in the art.

DESCRIPTION OF THE PREFERRED EMBODIMENT

Figure 1:
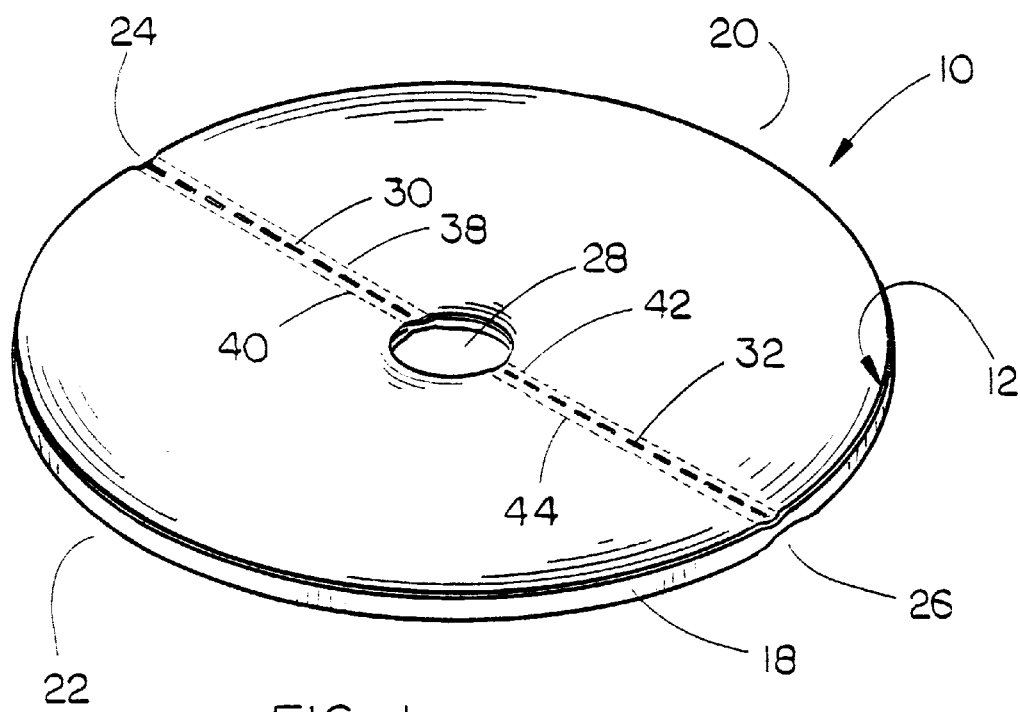
FIG. 1 is a perspective view of the breast pad of this invention.
Figure 2:
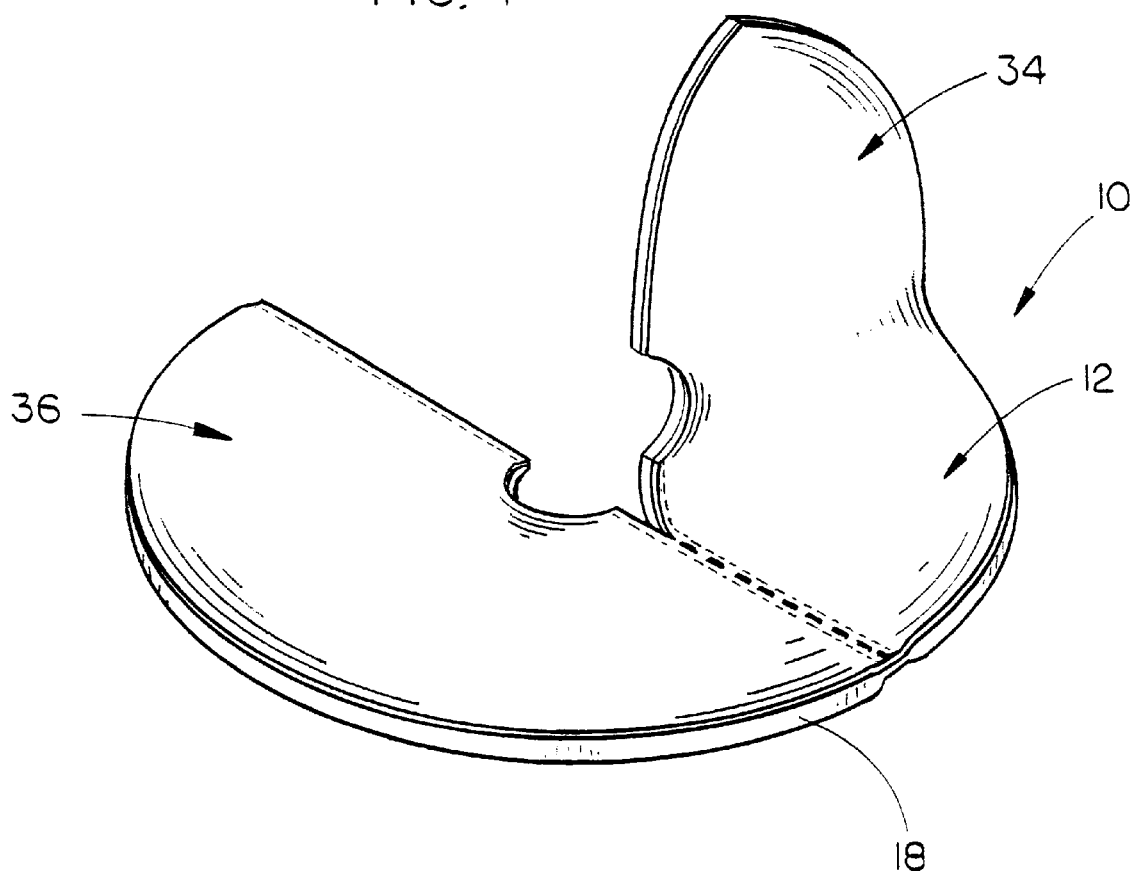
FIG. 2 is a perspective view of the breast pad being separated into two breast pad members.
Figure 3:
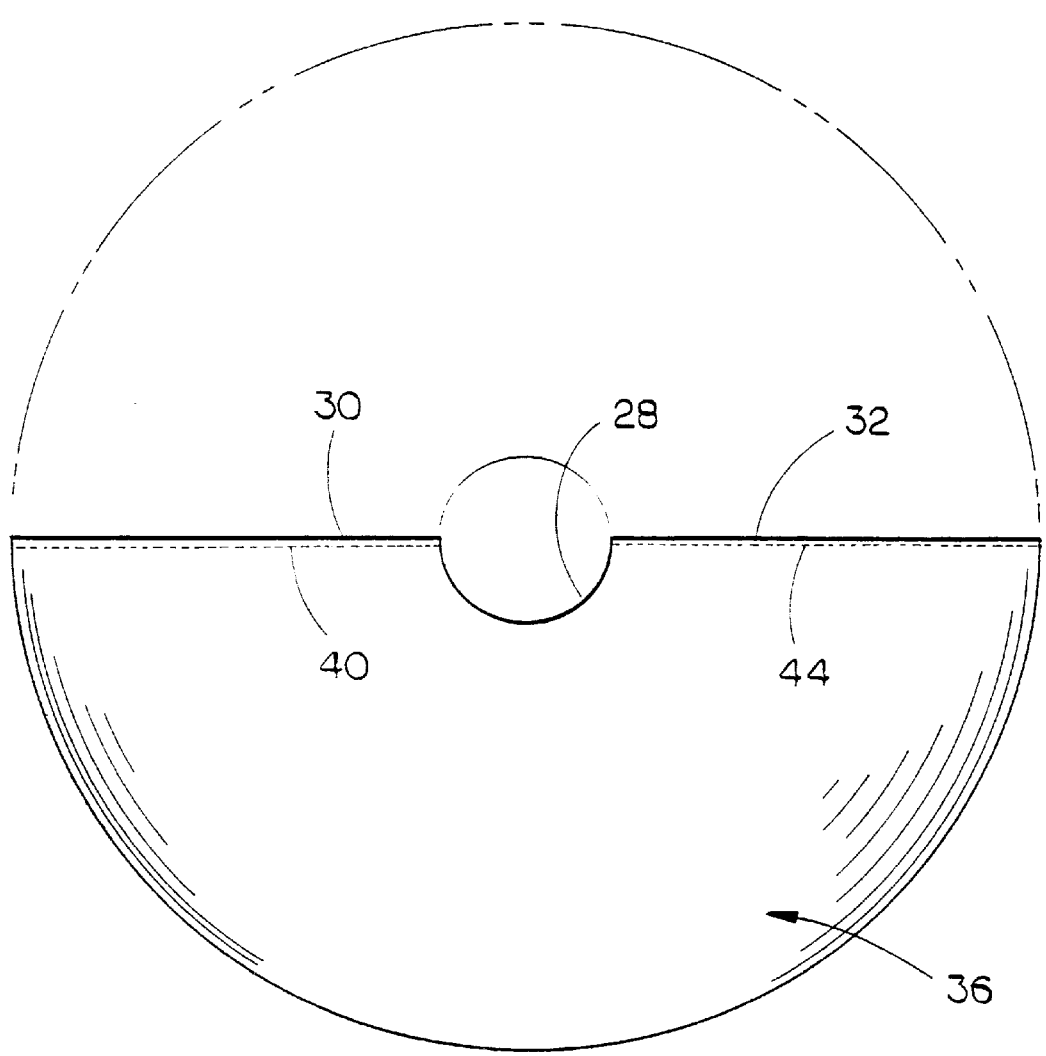
FIG. 3 is a top plan view of the one of the breast pad members.
Figure 4:
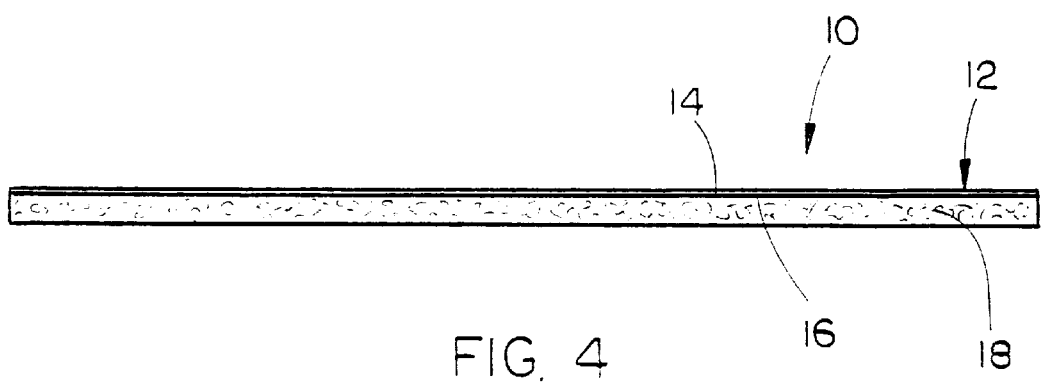
FIG. 4 is a sectional view of the breast pad.

The disposable therapeutic breast pad of this invention is referred to generally by the reference numeral 10 and includes a generally disc-shaped outer layer 12 having an outer surface 14 and an inner surface 16. A layer of an absorbent material 18 is positioned adjacent the inner surface 16 of outer layer 12 and is bonded thereto by any conventional means. Outer layer 12 is water-repellent or water-impervious and may be of any suitable material such as polyethylene. The absorbent layer may also be comprised of any suitable material such as a multi-ply tissue material such as that sold by Cel-Fibe Company (under the designation Absorbent Cel-Fibe Code 2001).

For purposes of description, breast pad 10 will be described as having an upper end 20, lower end 22, and opposite sides 24 and 26. Breast pad 10 is preferably provided with a central opening 28 formed therein for receiving the nipple of the female breast therein. Preferably, a perforated tear line 30 is provided in the breast pad 10 which extends between side 24 and the opening 28. If perforated tear line 30 is utilized, a perforated tear line 32 is also utilized which extends between side 26 and the central opening 28. The perforated tear lines 30 and 32 enable the breast pad 10 to be separated into two generally C-shaped breast pad members 34 and 36.

When the perforated tear lines 30 and 32 are utilized, it is preferred that upper and lower rows of stitching 38 and 40 extend through the breast pad 10 above and below the perforated tear line 30 and upper and lower rows of stitching 42 and 44 extend through the breast pad 10 above and below the perforated tear line 32. The upper and lower rows of stitching just described aid in providing a smooth separation of the breast pad 10 into the two C-shaped breast pad members 34 and 36 and also aid in maintaining the integrity of those breast pad members 34 and 36 after they have been separated. Further, the rows of stitching 38, 40, 42 and 44 also aid in preventing moisture contained in the absorbent material 18 from leaking or passing through the perforated tear lines.

In use, the breast pad member 10 is soaked in a measured amount of hot or cold tap water with the absorbent layer 18 absorbing the water. The breast pad 10, after being soaked in water, is then placed adjacent the female breast so that the nipple is received by the opening 28. The moisture-impervious outer layer 12 maintains the water within the absorbent layer 18 and prevents the water in the layer 18 from coming into contact with the brassiere which is normally positioned outwardly of the breast pad 10. When the warmth of the warm or hot water in the layer 18 has dissipated, the breast pad 10 may be removed from the female breast and discarded. The breast pad 10 may also be used to cool the breast by soaking the breast pad in a measured amount of cold tap water or ice water and then placing the breast pad 10 in the brassiere as described hereinabove.

If it is desired to utilize a single C-shaped breast pad member, the breast pad 10 is separated along the tear lines 30 and 32 to provide the two C-shaped breast pad members 34 and 36, so that less than the entire breast may be heated or cooled.

Thus it can be seen that a novel therapeutic breast pad has been provided for heating or cooling the female breast during nursing which accomplishes at least all of its stated objectives.

We claim:

1. A disposable therapeutic breast pad for heating or cooling the female breast during nursing, comprising:

a generally disc-shaped, moisture-impervious outer layer having inner and outer surfaces;

and an absorbent material disposed inwardly of said inner surface of said outer layer adapted to be soaked in hot or cold water for heating or cooling the female breast;

said outer layer and said absorbent material having an upper end, a lower end, and opposite sides;

and a perforated tear line extending between said opposite sides to permit the breast pad to be separated into two C-shaped breast pad members.

2. The disposable therapeutic breast pad of claim 1 wherein upper and lower rows of stitching extend through said outer layer and said absorbent material above and below said perforated tear line, respectively.

3. The disposable therapeutic breast pad of claim 1 wherein a generally circular-shaped opening is provided in the central portion of said outer layer and said absorbent material for receiving the nipple of the female breast.

4. A disposable therapeutic breast pad for heating or cooling the female breast during nursing, comprising:

a generally disc-shaped, moisture-impervious outer layer having inner and outer surfaces;

and an absorbent material disposed inwardly of said inner surface of said outer layer adapted to be soaked in hot or cold water for heating or cooling the female breast;

a generally circular-shaped opening being provided in the central portion of said outer layer and said absorbent material for receiving the nipple of the female breast;

said outer layer and said absorbent material having an upper end, a lower end, and opposite sides;

a first perforated tear line extending between one of said sides to said circular-shaped opening;

and a second perforated tear line extending between the other of said sides to said circular-shaped opening to permit the breast pad to be separated into two generally C-shaped breast pad members.

5. The disposable therapeutic breast pad of claim 4 wherein upper and lower rows of stitching extend through said outer layer and said absorbent material above and below said tear lines.

* * * * *